United States Patent
Pless

(10) Patent No.: US 6,641,612 B2
(45) Date of Patent: Nov. 4, 2003

(54) AMBULATORY BLOOD PUMP

(76) Inventor: Benjamin David Pless, 5 Ridgeview Dr., Atherton, CA (US) 94027

(*) Notice: Subject to any disclaimer, the term of this patent is extended or adjusted under 35 U.S.C. 154(b) by 36 days.

(21) Appl. No.: 10/005,492

(22) Filed: Dec. 4, 2001

(65) Prior Publication Data

US 2002/0128709 A1 Sep. 12, 2002

Related U.S. Application Data

(62) Division of application No. 09/349,892, filed on Jul. 8, 1999, now Pat. No. 6,342,071.

(51) Int. Cl.[7] ............................................. A61M 1/10
(52) U.S. Cl. ..................... 623/3.1; 623/3.27; 417/50; 600/16
(58) Field of Search ................. 623/3.1, 3.27; 600/16; 310/11; 417/50

(56) References Cited

U.S. PATENT DOCUMENTS

| | | |
|---|---|---|
| 3,633,217 A | 1/1972 | Lance |
| 4,908,012 A | 3/1990 | Moise et al. |
| 5,084,144 A | 1/1992 | Reddy et al. |
| 5,511,958 A | 4/1996 | Chen et al. |
| 5,668,420 A | 9/1997 | Lin et al. |
| 5,678,306 A | 10/1997 | Bozeman et al. |
| 5,685,698 A | 11/1997 | Smoll |
| 5,786,439 A | 7/1998 | Van Antwerp et al. |
| 5,803,720 A | 9/1998 | Ohara et al. |

*Primary Examiner*—Bruce Snow
(74) *Attorney, Agent, or Firm*—Jay A. Chesavage

(57) ABSTRACT

A blood pump intended to be carried by a freely moving patient uses perpendicular magnetic and electrical fields to propel blood. A rod mounted coaxially inside a tube has electrodes in blood contact for establishing a radial electric field, and an inductor having windings parallel to the axis of the tube is used to establish a circumferential magnetic field. To avoid the evolution of gas at the electrode surfaces the magnetic and electric fields are periodically reversed, and the electrodes are made to have very high surface areas. The blood pump is powered by batteries or fuel cells (or a combination of both) to provide long service between recharging and to reduce the weight carried by the patient.

28 Claims, 8 Drawing Sheets

Section b-b

Section c-c

Section c-c

Section c-c

AMBULATORY BLOOD PUMP

This application is a division of application Ser. No. 09/349,892 filed on Jul. 8, 1999 and now U.S. Pat. No. 6,342,071.

BACKGROUND OF THE INVENTION

This invention pertains to an improved ambulatory blood pump, which means a blood pump carried by a freely moving patient, either internally (implanted) or outside the body. It may take any form including left ventricular assist device, bi-ventricular assist device, right ventricular assist device, or total artificial heart.

Patients who have experienced severe heart failure are often considered candidates for heart transplantation. However, the number of people who need a heart transplant far exceeds the number of donor hearts available. As a result, mechanical blood pumps are used to sustain patients until a donor heart is available (e.g. "bridge to transplant"). Ultimately the clinical goal is to develop a blood pump small enough and reliable enough to serve as a chronic organ replacement for patients with heart failure, obviating the need for heart transplants in many cases.

Currently available blood pumps use mechanical mechanisms to move the patient's blood. Typical technologies include pusher-plate (for example U.S. Pat. No. 5,511,958), centrifugal (for example U.S. Pat No. 5,803,720), and turbine or axial flow (for example U.S. Pat. No. 4,908,012). As described in U.S. Pat. No. 5,678,306 a major concern is damage to the blood cells from the pump. Smoll (U.S. Pat. No. 5,685,698) suggests the use of the Lorentz force to propel the blood with a pump having no moving parts. As he notes, similar technology has been applied to the propulsion of marine vessels as exemplified in U.S. Pat. No. 5,668,420. However, the efficiency of a pump using the Lorentz force is lower than mechanical pumps. Furthermore, in the Smoll patent the electrodes are not in direct blood contact, further impairing the transfer of electrical energy to blood motion.

Currently available ambulatory blood pumps often use a combination of an implanted battery and an external battery pack. The patient has to recharge the batteries frequently to keep the pump working. Furthermore, the external batteries are heavy, and are a significant burden to a patient with compromised cardiac function. To overcome the lower efficiency of a blood pump using the Lorentz force, and to provide the patient with a more easily portable power supply, the subject invention employs fuel cells as a means of storing energy.

Therefore it is a purpose of this invention to provide an improved ambulatory blood pump having no moving parts; and it is a further a purpose of this invention to provide an improved power source for ambulatory blood pumps.

SUMMARY OF THE INVENTION

This patent describes an improved ambulatory blood pump. The pump has no moving parts and operates by the application of the Lorentz force on the blood. Electrodes in direct blood contact are employed to improve electrical energy transfer to blood motion. High surface area electrodes, electrode coatings, electrode shape and time varying electrical and magnetic fields are used to diminish the effects of electolysis that would otherwise generate gas bubbles. It is recognized that the electrical efficiency of a pump using the Lorentz force is lower than a mechanical pump, and a novel energy source employing fuel cells is used to overcome the deficiency. The same energy source can also be used advantageously to reduce the weight of conventional ambulatory blood pumps.

A first object of the invention is a blood pump comprising a magnetic field and an electric field whereby blood is pumped by a Lorentz force. A second object of the invention is a blood pump wherein the electrodes have an enhanced surface area for the reduction of gas evolution at the electrode surface area. A third object of the invention is a blood pump were the polarity of the voltage applied to the electrodes and the polarity of the magnetic field are reversed to reduce gas evolution from the elecrodes. A fourth object of the invention is a blood pump powered by fuel cells. A fifth object of the invention is a blood pump having a fuel cell which has charge provided non-invasively through a biological barrier such as living tissue.

DESCRIPTION OF THE DRAWINGS

FIG. 1b is an axial cross section of the blood pump shown in FIG. 1a.

FIG. 1c is a radial cross section of the blood pump shown in FIG. 1a.

FIG. 2b is an axial cross section of the blood pump of FIG. 2a.

FIG. 2c is a radial cross section of the blood pump of FIG. 2a.

FIG. 4b shows the electrical waveforms produced by the pump controller of FIG. 4a.

FIG. 5b shows the electrical waveforms produced by the pump controller of FIG. 5a.

DETAILED DESCRIPTION OF THE INVENTION

Figure 1A:
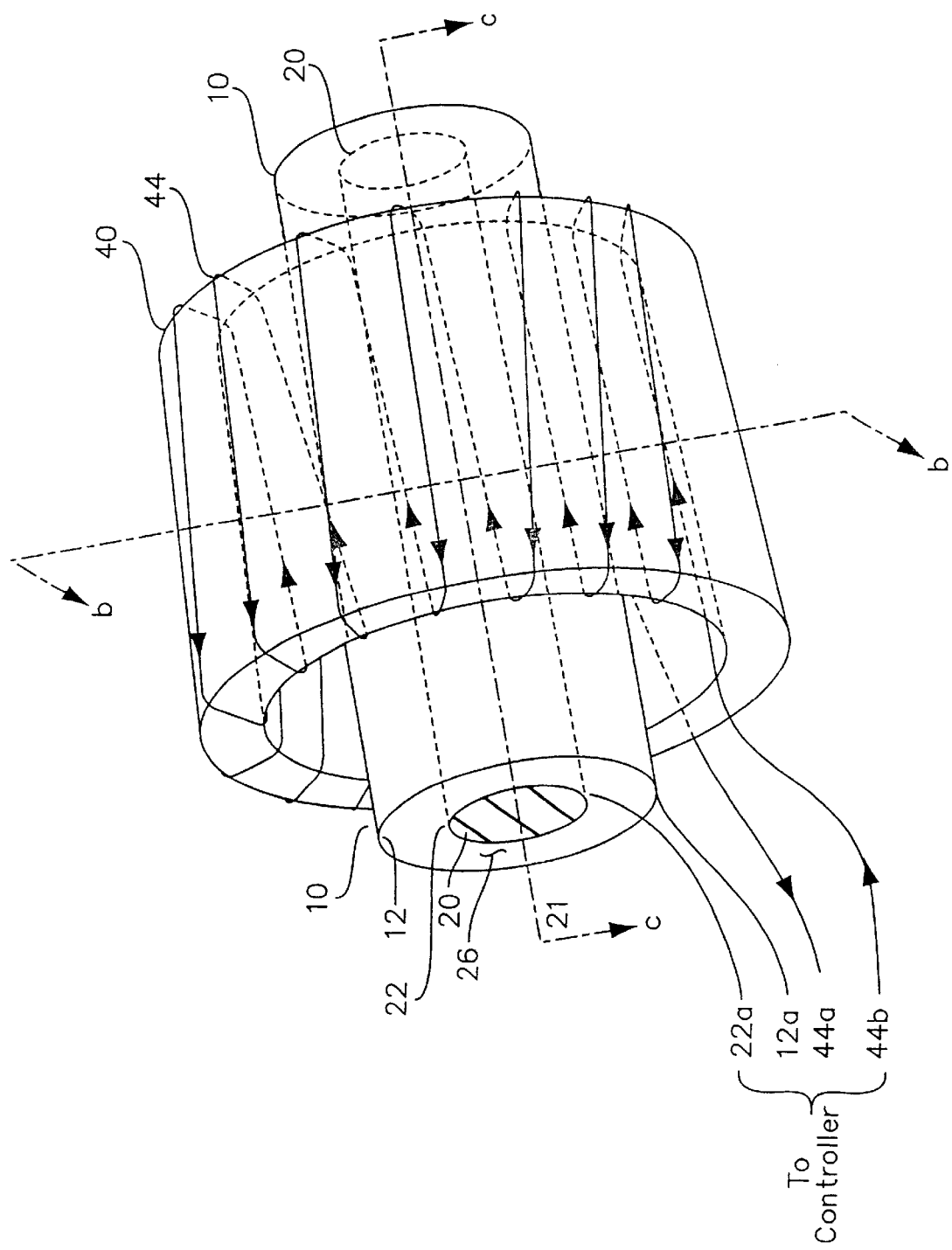
FIG. 1a is a perspective drawing of a blood pump having windings external to a conduit.
Figure 1B:
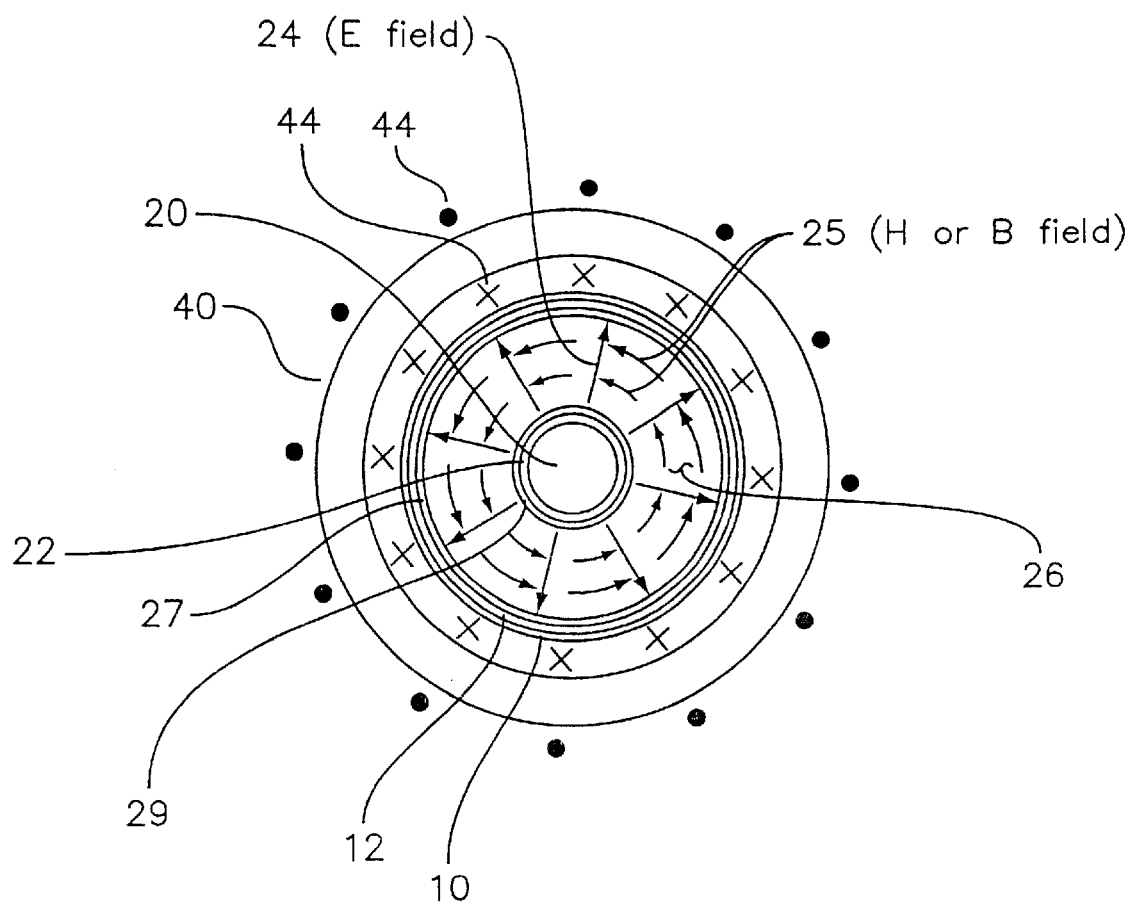
Figure 1C:
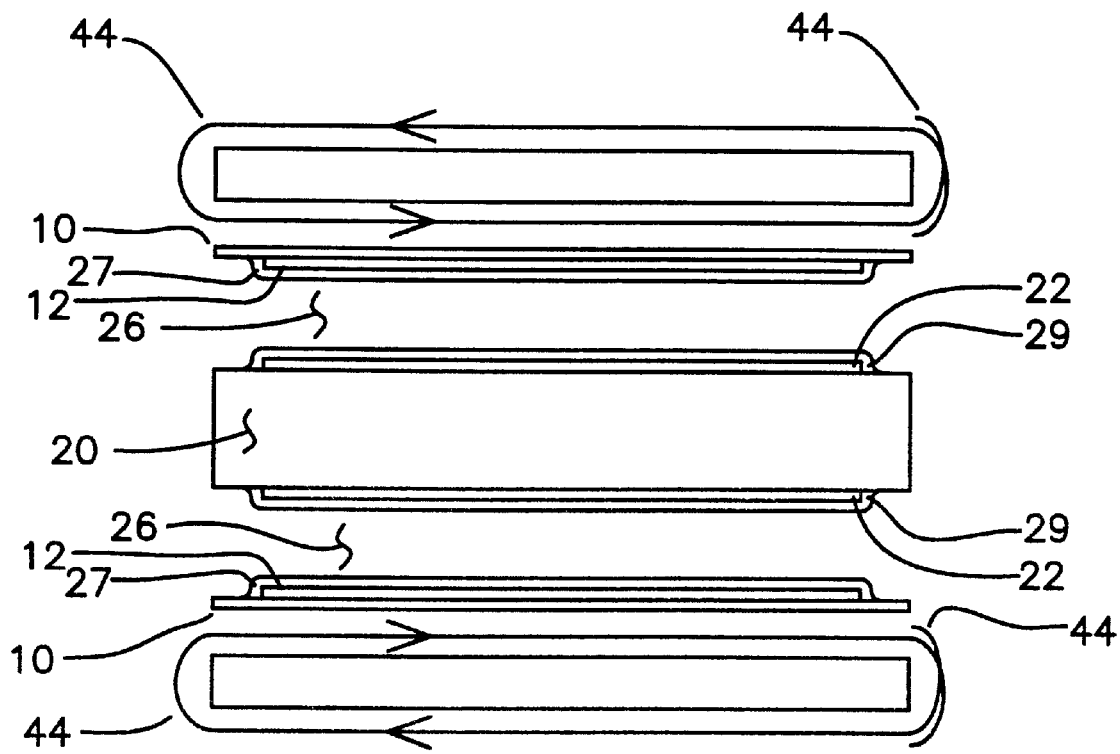

A diagram of the improved blood pump is shown in FIGS. 1a–1c. In FIG. 1a, there is a conduit 10, shown here as a tube, having an electrode 12 incorporated in it, and in direct blood contact for at least a part of its length. Running coaxially in the middle of the conduit is a central shaft 20, shown here as a rod having an axis 21, that also has an electrode 22 incorporated in it and is in direct blood contact for at least part of its length. A channel 26 in which blood can flow is thereby established between the conductive inner surface 12 of the conduit 10, and the conductive outer surface 22 of the central shaft 20.

An inductor body 40 is disposed coaxially around, and outside of a conduit 10. The windings 44 of the inductor body 40 run parallel to the axis of the conduit 10, and have leads 44b and 44a for the application of a current. The use of a material for the form 40 with a low permeability is desired to prevent field concentration within the form 40, which would lower the B field available in channel 26. Form 40 should also be chosen to have low eddy current losses, so that changing magnetic fields are not absorbed by the form 40. The arrows in FIG. 1b of winding 44 are shown to aid in the understanding of the magnetic field developed through the application of a current, although the polarity of this current may be changed from that shown in the FIGS. 1a–c. When electrical current is caused to flow in the inductor windings 44, a magnetic field is established which runs circumferentially in the channel 26. FIG. 1b is the axial section b—b of FIG. 1a, and shows the windings 44 represented with a dot to indicate a current flowing out of the page, and an X to represent current flowing into the page. The resulting circumferential field 25 is shown by the series of arrows indicating the magnetic field magnitude and direction. Furthermore, when an electrical potential is applied to the two electrodes 12 and 22 via associated leads 12a and 22a, a radial electric field 24 is established in the channel 26 perpendicular to the magnetic field, as shown in FIG. 1b. Since the blood is a conductive electrolyte, the simultaneous application of perpendicular magnetic and electric fields results in a Lorentz force on the blood causing it to move along axis 21 in the channel 26, enabling the subject invention to operate as a blood pump. The direction of blood flow depends on the direction of the magnetic field, and the polarity of the electrical potential. If the polarity of the electric potential applied to electrodes 12 and 22 is reversed at the same time that the direction of the magnetic field is reversed (by changing the direction of current flow in the windings 44), the direction of blood flow remains unchanged. This reversal of polarity may occur at regular periods, or irregular temporal intervals.

The conduit 10 and the central shaft 20, as well as the electrodes 12 and 22 are made of non-magnetic materials to avoid affecting the magnetic field in the channel. Preferred materials are titanium or platinum, and thin depositions of these conductive materials may be desirable to reduce eddy current losses in the presence of changing magnetic fields.

In prior art systems, intended for marine vehicle propulsion (e.g. U.S. Pat. No. 5,668,420), fixed anode and cathode voltages are used. Large DC currents are caused to flow between the anode and cathode in the presence of a magnetic field to generate thrust. As a result there is both significant joule heating, which might be undesirable in a blood pump, but more importantly significant volumes of gas can evolve at the electrodes by the well-known process of electrolysis. The consequences of gas bubble generation in a blood pump used for clinical purposes include embolism and stroke. Therefore it is critical to avoid the generation of bubbles in a blood pump.

Figure 1D:
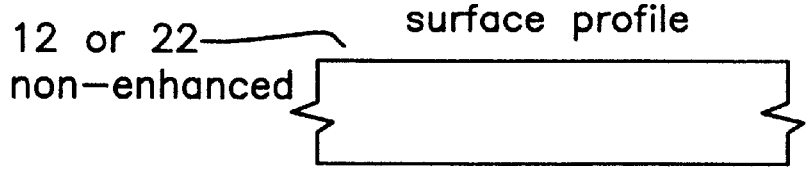
FIG. 1d is the surface profile view of an electrode having an enhanced surface and non-enhanced surface.
Figure 1D:
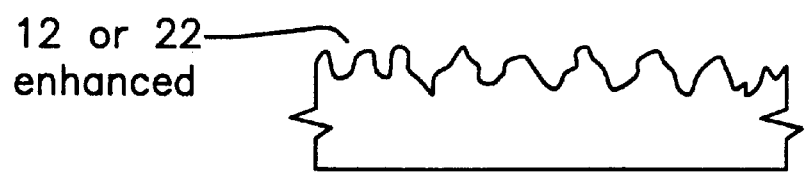

The subject invention primarily uses two techniques to avoid the evolution of gas at the electrodes 12 and 22. First, the electrodes 12 and 22 are highly textured at a microscopic scale to allow a comparatively large electric field to be imposed on the blood while still maintaining a low current density at the actual electrode-to-electrolyte interface. FIG. 1d shows the surface profiles of electrodes 12 or 22 in their non-enhanced and enhanced states. The ratio of enhanced surface area after treatment to non-enhanced surface area before treatment is known as the surface area enhancement ratio. This surface area enhancement serves to make the enhanced surface areas of the inner and outer surfaces closer to each other in size, so that the electric field density on the electrode with the smaller surface area is closer to the electric field density of the electrode having the larger surface area. Best operation may occur when the ratio of first electrode enhanced surface area to second electrode enhanced surface area is in the range of 0.5 to 2. The preferred technique for achieving a biocompatible, high surface area on the electrodes is to apply a coating capable of achieving a very fine microscopic structure such as iridium oxide, titanium nitride, or platinum black, although other techniques such as etching, machining, or grit blasting can also be used to enhance the surface area through pitting. Iridium oxide, titanium nitride and platinum black can achieve surface area enhancement ratios of 10 to 100 or more.

To provide long term biostability of the high surface area electrodes 12 and 22, and to reduce the incidence of thrombosis a protective coating 27 and 29 may be applied to the surface, as shown in FIG. 1c. Depositable ion exchange membranes such as Nafion® (from Dupont; the method for dissolving Nafion® for deposition is found in U.S. Pat. No. 5,084,144) or a biocompatible hydrogel such as that disclosed in U.S. Pat. No. 5,786,439 may be used. The protective coatings 27 and 29 assure that the high surface area interface between the electrode surface and the electrolyte does not degrade after long exposure to blood. It should be understood that the protective coatings 27 and 29 are conductive (by allowing ion flow); therefore the electrodes 12 and 22 are in blood contact even if protected by the protective coating 27.

The second method employed by the subject invention to avoid the evolution of gas bubbles at the electrodes is to reverse the potentials applied to the electric field conductors 12 and 22. Periodically reversing the electrode potentials produces an improved result over the fixed anode and cathode employed in the prior art U.S. Pat. No. 5,668,420.

Figure 2A:
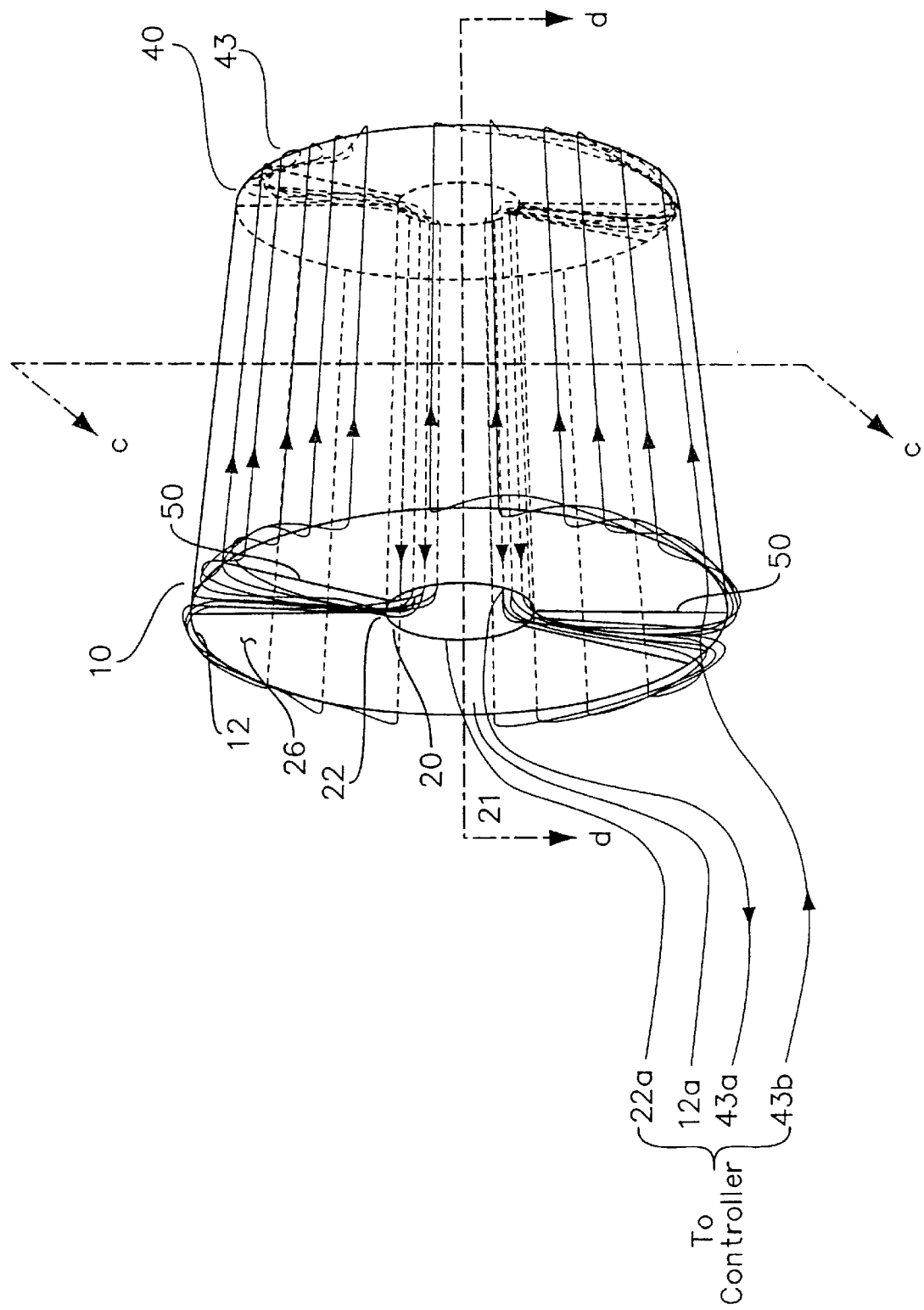
FIG. 2a is a perspective drawing of a blood pump having windings internal to and external to a channel.
Figure 2B:
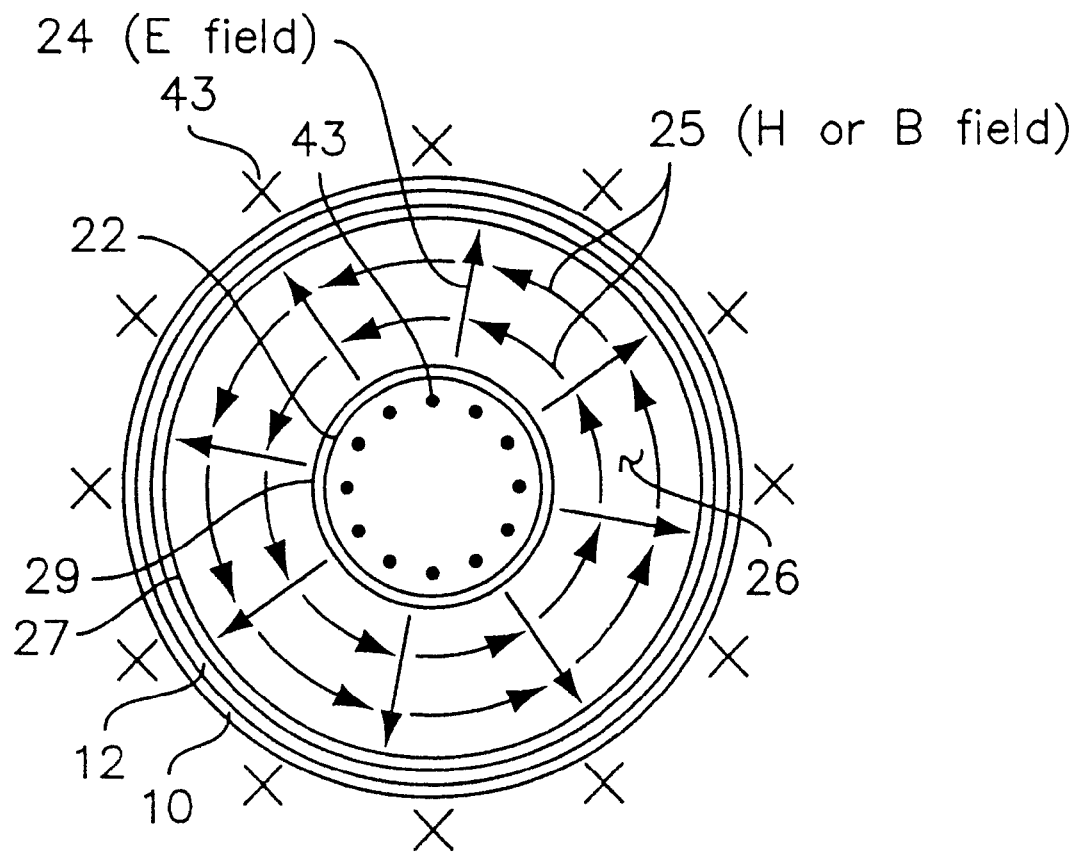
Figure 2C:
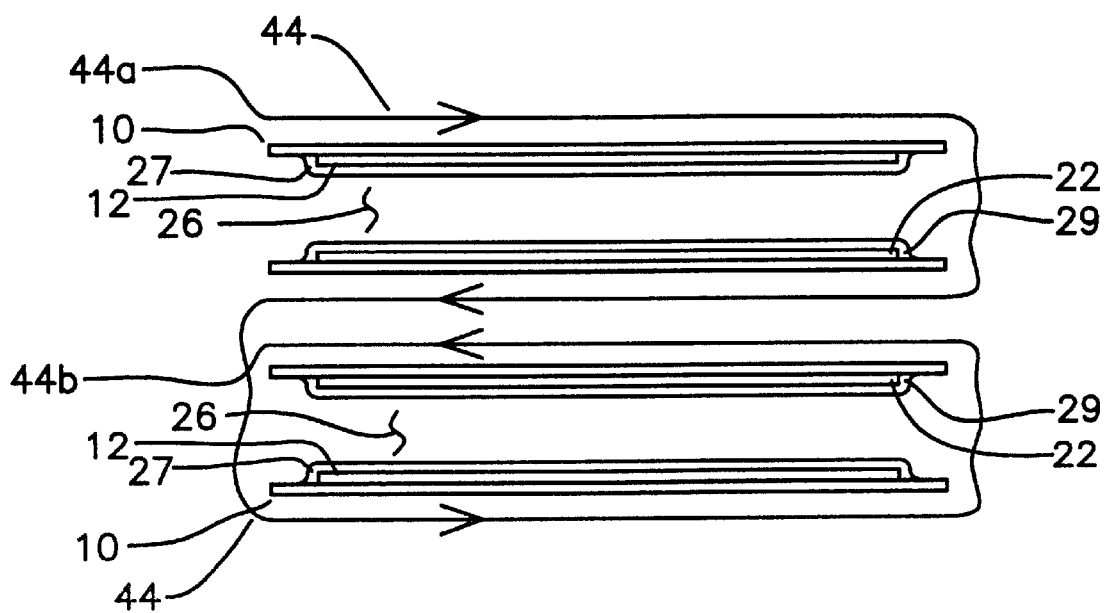

FIG. 2a shows an alternate embodiment of a blood pump. In this embodiment, the conduit 10 having an inner electrode 12, and rod 22 having an outer electrode 22 are similar to those of FIG. 1a. Wire 43 is now repetitively wound outside the conduit 10, and through the middle of core 20. Supports 50 also serve to gather and isolate conductors 43 from blood flowing in channel 26 which would otherwise encounter these individual conductors. It is possible to use varying numbers of supports 50 and different groupings of conductors 43. FIG. 2b shows the radial view of these conductors, and as earlier, the dots and Xs indicate the current flow and sense in conductor 43. The embodiment of FIG. 2a has the advantage over FIG. 1a of using the magnetic field produced by both senses of conductor 43 to produce magnetic field 25. FIG. 2c also shows the arrangement of windings and other elements of the pump of FIG. 2a. It is clear to one skilled in the art that there are many arrangements of conductors for the production of a magnetic field and an electric field that are mutually orthogonal to the direction of blood flow in a channel. The figures shown here are but two examples of such arrangements of wires and electrodes in a blood flow channel, and the examples used herein are not intended to limit those arrangements to only those described.

To maximize the electrical potential that can be imposed without evolving gas, the current densities at the surfaces of the two electrodes 12 and 22 can be matched. As is clear from FIGS. 1b and 2b, the inner electrode 22 is smaller than the outer electrode 12, and will experience a higher current density for a given electrical potential imposed between the two electrodes 22 and 12. At the microscopic level, balancing the current densities of the two electrodes 22 and 12 is achieved in this invention by having different amounts of surface area enhancement on the electrodes 22 and 12, as shown in FIG. 1d. Given the same linear electrode length without surface enhancement, the surface areas of the inner electrode 22 and outer electrode 12 have the same ratio as their respective diameters (for a system having a circular cross-section). Therefore, for example, if the diameter of the central shaft 20 is one centimeter, and the diameter of the conduit 10 is two centimeters, then the surface enhancement ratio of the inner electrode 22 would be 2 to achieve the same current density for both electrodes 22 and 12.

Figure 3A:
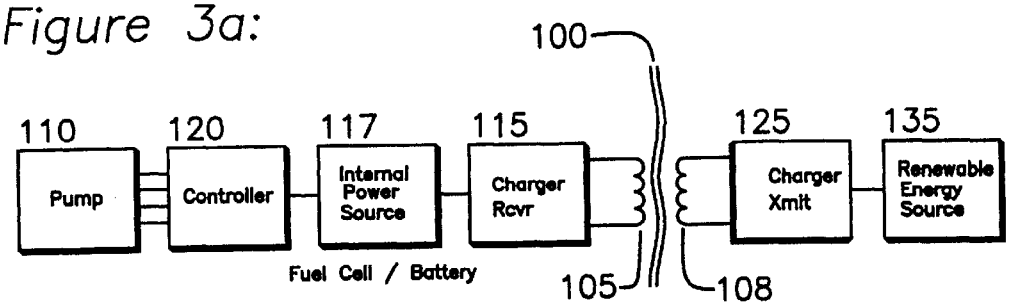
FIG. 3a is a block diagram of a power system for an ambulatory blood pump using a completely implanted power source which may comprise a fuel cell or a rechargeable battery.
Figure 3B:
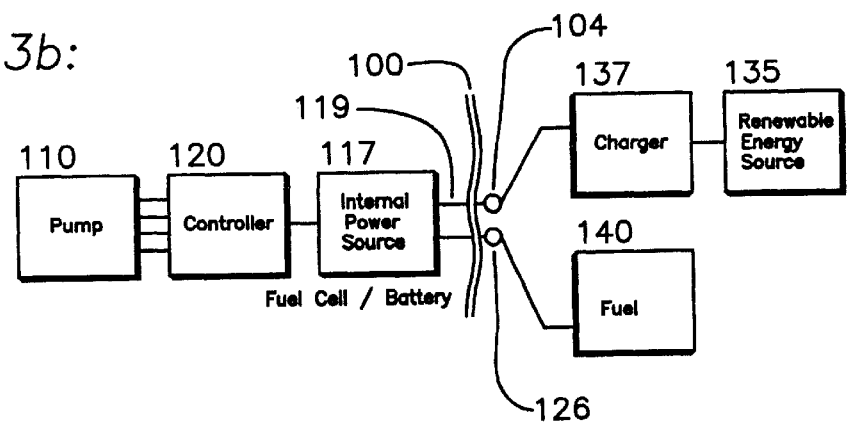
FIG. 3b is a block diagram of a power system for an ambulatory blood pump using an implanted power source which may comprise a fuel cell or a rechargeable battery, wherein the power source communicates with a plurality of external chargers through a transcutaneous port.

The advantages of the blood pump described above include reduced hemolysis (blood cell damage), and the reliability inherent in a machine having no moving parts. A disadvantage however is, that at this time, the energy efficiency of a pump using the Lorentz force to move blood is lower than conventional mechanical blood pumps. As a result, this invention includes a novel energy storage device using fuel cells for powering blood pumps. Fuel cells are capable of achieving over ten times the stored energy of a battery of equivalent size. In an ambulatory blood pump that means that the patient can go much longer before needing to charge the energy storage device powering their pump; and also results in a much lighter energy storage device, improving portability. As shown in FIGS. 3a and 3b, there are several configurations for the use of a fuel cell to power a blood pump.

FIG. 3a shows a system having an implanted blood pump 110, a controller 120 for regulating power going to the pump, and for adjusting the pumping speed as needed. Internal power source 117 may be a miniature version of the proton exchange membrane type, and is adapted for use in an implantable environment. Unlike most fuel cells, it is completely sealed, and during the charging cycle it separates water into hydrogen gas and oxygen gas for subsequent use as fuel in the generation of electricity. An alternative internal power source 117 could be a rechargeable battery, of the lithium-ion type which powers the pump for periods of time when the external charger-transmitter 125 is not available. The charger receiver 115 charges the internal power source 117, and receives power from a coil 105 which acts as the secondary of a power transformer having its primary coil 108 on the outside of the skin barrier 100. A renewable energy source 135 is carried by the patient, and supplies power to the charger transmitter 125 that drives the coil 108. The renewable energy source 135 is either a conventional arrangement of rechargeable batteries (such as nickel-cadmium, lithium-ion, or metal hydride), or preferably is a miniature fuel cell for reduced size, weight, and increased duration between recharging cycles. An additional advantage of using a miniaturized, portable fuel cell (instead of a rechargeable battery) for this application is that a fuel cell can be replenished very quickly by refueling, as compared to the longer charge times required for a rechargeable battery.

FIG. 3b shows a system equivalent to the one described above for FIG. 3a, except that the fuel cell 117 is connected to a transcutaneous electrical port 104, or fuel cell connection 126. The electrical port 104 allows charging of the fuel cell 117 by a charger 137, and fuel connection 126 allows replacement of the fuel cell fuel (preferably methane) from a fuel supply 140, or both forms of charging may be employed.

It should be understood that the energy storage systems depicted in FIG. 3 using fuel cells (either implanted or extracorporeal) can also advantageously use fuel cells in combination with rechargeable batteries, or capacitors, for additional energy management flexibility without detracting from the intent of this invention. While the motivation for the novel energy storage system described herein arose from the increased energy needs of a blood pump using the Lorentz force, it is applicable to any ambulatory blood pump system, and will result in the significant advantage to the patient of a smaller, lighter more portable life support system.

Figure 4A:
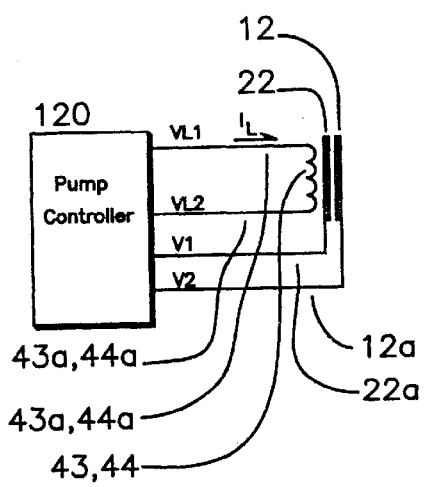
FIG. 4a shows the electrical connections between a pump and a pump controller.
Figure 4B:
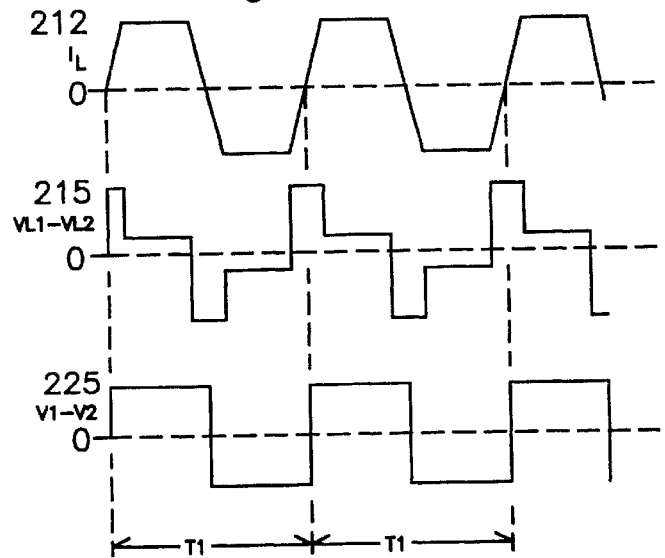

The details of pump controller 120 are shown in FIG. 4a. Pump controller 120 has outputs 43a, 44a and 43b, 44b for driving the inductor, and outputs 12a and 22a for driving the electrodes. For example, as shown in FIG. 4b, the voltage waveform 215 produces the current waveform 212, which drives the inductor 43 or 44, and the voltages applied to electrodes 12 and 22 of this invention are not fixed in time. Instead they vary synchronously at a rate which is rapid compared to the rate that a heart beats. Since maximum heart rate is about 5 hertz, T1 of FIG. 4b is typically shorter than 6 ms. As a result, neither electrode is an electrically fixed anode or cathode. As the direction of the electrical field reverses cycle to cycle, the electrode that previously was the anode becomes the cathode, and vice versa. Note that the direction of blood flow does not reverse cycle to cycle, because the electric and magnetic fields reverse direction in unison.

Figure 5A:
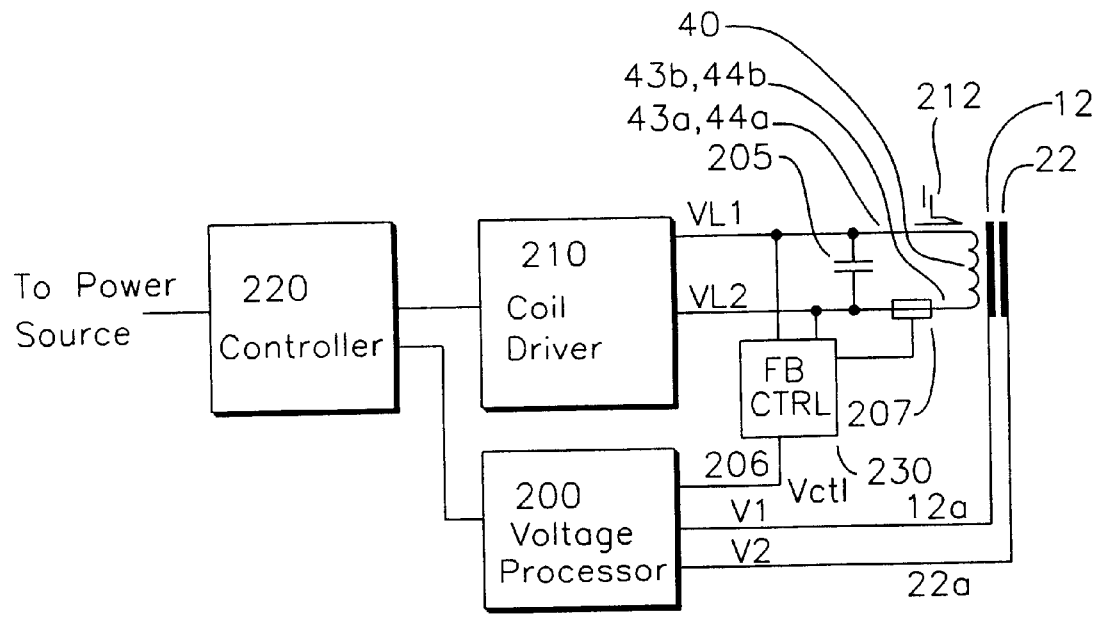
FIG. 5a shows the electrical connections between a pump and a pump controller for resonant current operation.
Figure 5B:
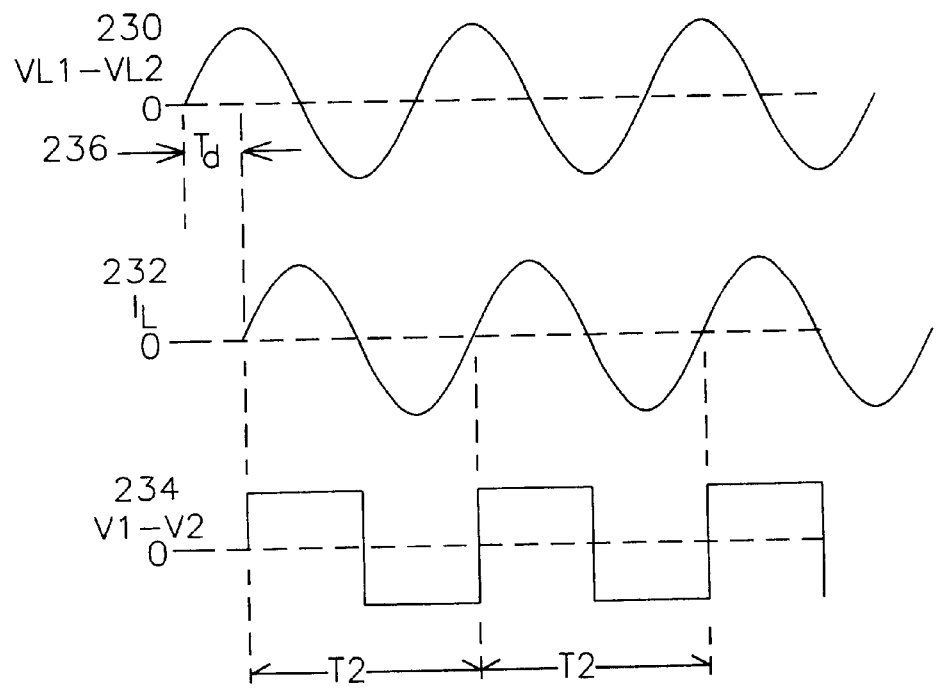

The preferred embodiment of the controller 120 of the ambulatory blood pump of this patent is shown in FIG. 5a and 5b. A coil driver 210 drives the inductor 40, which is in resonance with a capacitor 205. A low resistance conductor, preferably fabricated of silver, or a high temperature superconductor, is utilized to form the windings 43 or 44 of the inductor 40. Feedback 206 is derived either directly from the current measured by sensor 207, or it is derived from the voltage applied across capacitor 205. This information provided by feedback controller 230 is used to provide electrode voltages 12a and 22a which are in phase with the inductor current. The advantage of operating the inductor 40 in resonance is the low power required to maintain the magnetic field generated by the inductor 40. FIG. 5b shows the waveforms for circuit operating in resonance. Inductor voltage 230 is produced by coil driver 210, which causes magnetic field generator 40 and capacitor 205 to resonate, producing the inductor and capacitor voltage shown as curve 230. The measured voltage could be delayed an interval Td 236 to estimate the time of inductive current sense change, or the inductor current $I_L$ 212 could be directly measured, as shown in inductor current waveform 232. The electrode voltage 234 is generated by a voltage processor 200 and is applied to the electrodes 12 and 22, alternating in polarity as the inductor current changes polarity, as shown in curves 232 and 234. The electrode voltage 234 is shown as a square wave, although it could be sinusoidal, or any waveform intended to minimize the evolution of gas at the electrodes 12 and 22. The controller 220 communicates with the coil driver 210 to set the inductor current $I_L$ 212; and communicates with the voltage processor 200 to set the electric field 225. The controller 220 can adjust the rate of blood flow by either adjusting the electrical field 234 generated by the voltage processor 200, or by varying the inductor current 232. The blood flow may be adjusted to be at a rate which is relatively continuous over a time scale of multiple heart beats; or the blood flow may be adjusted to be pulsatile within the time frame of a heart beat to mimic normal heart functionality.

Period T2 of FIG. 5b may be determined from the resonance formula $$F = \frac{1}{2\pi\sqrt{LC}}$$

where F is the resonance frequency,
L is the inductance of inductor 40,
and C is the capacitance of capacitor 205.

Described herein is an ambulatory blood pump having no moving parts (to enhance reliability and reduce hemolysis), further utilizing a novel energy source applicable to any ambulatory blood pump, and having additional features to minimize thrombosis and provide blood flow rate control. It should be understood that the invention is not limited by the specific embodiment described, but that various configurations are intended to be included within the scope of the invention including arbitrary cross-sectional shapes and dimensions, as well as various linear shapes and dimensions best suited to the patient's anatomy, and the possibility of multiple conduits as opposed to the single conduit detailed here.

I claim:

1. A blood pump comprising:
    a conduit having a front surface, a rear surface, an inner electrically conductive surface and an outer surface, said conductive inner surface forming a first electrode;
    a rod having an inner channel, a central axis, a front surface located near said conduit front surface and a rear surface located near said conduit rear surface, and an electrically conductive outer surface forming a second electrode;
    a blood flow channel formed by said rod outer surface and said conduit inner surface;
    a current-carrying conductor applied to the inner channel and outer surface of said conduit, said conductor applied such that current flowing in said conductor flows parallel to said central axis from said rod inner channel front to said rod inner channel rear, and thereafter said current flows parallel to said central axis and from said conduit outer surface rear to said conduit outer surface front;
    a voltage source connected between said first electrode and said second electrode;
    a current source furnishing current through said current carrying conductor.

2. The blood pump of claim 1 wherein said voltage source produces a fixed voltage and said current source produces a fixed current.

3. The blood pump of claim 1 wherein said voltage source and said current source temporally reverse polarity at substantially the same time.

4. The blood pump of claim 3 wherein said reversal of polarity occurs at a rate faster than the heart rate.

5. The blood pump of claim 1 wherein said voltage source and said current source periodically reverse polarity at substantially the same time.

6. The blood pump of claim 5 wherein at least one of said voltage source and said current source produce square waves.

7. The blood pump of claim 5 wherein at least one of said voltage source and said current source produce sinusoidal waves.

8. The blood pump of claim 7 wherein said current source produces said sinusoidal waves by driving a pump load comprising a capacitor either in series or in parallel with said current carrying conductor, said conductor and said capacitor forming a resonant circuit having a resonant frequency, and said sinusoidal waves are applied at said resonant frequency.

9. The blood pump of claim 8 wherein said current carrying inductor includes a sense measurement for determining the direction of said current, said voltage source using said sense measurement to determine when to periodically reverse said voltage polarity.

10. The blood pump of claim 1 wherein at least one of said electrodes has an enhanced surface area.

11. The blood pump of claim 10 wherein the ratio of said first enhanced electrode surface area to said second enhanced electrode surface area is within the range of 0.5 to 2.

12. The blood pump of claim 10 wherein said enhanced surface area comprises a texturing of said rod outer surface.

13. The blood pump of claim 10 wherein said enhanced surface area comprises the application of iridium oxide to said rod outer surface.

14. The blood pump of claim 10 wherein said enhanced surface area comprises the application of titanium nitride to said rod outer surface.

15. The blood pump of claim 10 wherein said enhanced surface area comprises the application of platinum black to said rod outer surface.

16. The blood pump of claim 10 wherein said enhanced surface area comprises pitting the surface of said rod outer surface.

17. The blood pump of claim 1 wherein said first electrode and said second electrode have a protective surface.

18. The blood pump of claim 17 wherein said protective surface comprises an ion exchange surface.

19. The blood pump of claim 18 wherein said ion exchange surface comprises Nafion.

20. The blood pump of claim 1 wherein said current source and said voltage source are powered by a fuel cell.

21. The blood pump of claim 20 wherein said fuel cell is a proton exchange membrane cell.

22. The blood pump of claim 21 wherein said fuel cell is locatable external to a patient.

23. The blood pump of claim 22 wherein said fuel cell and said pump are locatable entirely within a patient and said fuel cell is coupled to an external power source through electrical energy transfer means.

24. The blood pump of claim 23 wherein said energy transfer means includes an inductor locatable inside said patient and an inductor locatable outside said patient.

25. The blood pump of claim 1 wherein the output of said pump is controlled by at least one of said voltage source or said current source.

26. An ambulatory blood pump comprising:
    a pump for the movement of blood;
    a controller for controlling said pump;
    a power source for said pump and said controller, said power source comprising a fuel cell;
    a charge replenishment means for said fuel cell;
    wherein said replenishment means comprises a transcutaneous fuel cell refueling port whereby said fuel cell receives said fuel from an external replenishment source.

27. An ambulatory blood pump comprising:
    a pump for the movement of blood;
    a controller for controlling said pump;
    a power source for said pump and said controller, said power source comprising a fuel cell;
    a charge replenishment means for said fuel cell;
    wherein said replenishment means comprises a transcutaneous electrode for the transfer of charge from an external power source to said fuel cell.

28. An ambulatory blood pump comprising:
    a pump for the movement of blood;
    a controller for controlling said pump;
    a power source for said pump and said controller, said power source comprising a fuel cell;
    a charge replenishment means for said fuel cell;
    wherein said replenishment means comprises a subcutaneous inductor coupled to an external inductor for the transfer of charge from an external power source to said fuel cell.

* * * * *